(12) United States Patent
Pasternak et al.

(10) Patent No.: US 10,092,279 B2
(45) Date of Patent: Oct. 9, 2018

(54) SYSTEM AND METHODS FOR PROCESSING A BIOPSY SAMPLE

(71) Applicant: UC-CARE LTD., Yokneam (IL)

(72) Inventors: Alex Pasternak, Tel Aviv (IL); Tomer Schatzberger, Tel Aviv (IL); Shaike Schatzberger, Haifa (IL); Moshe Ebenstein, Haifa (IL)

(73) Assignee: UC-CARE LTD., Yokneam (IL)

( * ) Notice: Subject to any disclaimer, the term of this patent is extended or adjusted under 35 U.S.C. 154(b) by 364 days.

(21) Appl. No.: 14/775,415

(22) PCT Filed: Mar. 13, 2014

(86) PCT No.: PCT/IL2014/050262
§ 371 (c)(1),
(2) Date: Sep. 11, 2015

(87) PCT Pub. No.: WO2014/141262
PCT Pub. Date: Sep. 18, 2014

(65) Prior Publication Data
US 2016/0030021 A1 Feb. 4, 2016

Related U.S. Application Data

(60) Provisional application No. 61/791,350, filed on Mar. 15, 2013.

(51) Int. Cl.
*G06T 7/00* (2017.01)
*A61B 10/04* (2006.01)
(Continued)

(52) U.S. Cl.
CPC ............ *A61B 10/04* (2013.01); *A61B 8/0841* (2013.01); *A61B 8/12* (2013.01); *A61B 8/4254* (2013.01);
(Continued)

(58) Field of Classification Search
CPC ....... G06T 7/0012; G06T 7/0014; G06T 7/70; G06T 7/80; A61B 6/5247; A61B 6/5294;
(Continued)

(56) References Cited

U.S. PATENT DOCUMENTS

| 6,019,725 A | 2/2000 | Vesely et al. ................. 600/447 |
| 7,179,219 B2 | 2/2007 | Matlock ......................... 600/29 |

(Continued)

FOREIGN PATENT DOCUMENTS

| EP | 1335270 A1 | 8/2003 | ............... G06F 3/00 |
| EP | 1864624 A1 | 12/2007 | ............. A61B 19/00 |

(Continued)

*Primary Examiner* — Andrew W Johns
(74) *Attorney, Agent, or Firm* — Dorsey & Whitney LLP

(57) ABSTRACT

A system further comprises a processing unit functionally associated with the display, wherein the processing unit comprises an image processing module. The system further comprises a camera functionally associated with the processing unit via a communication channel for transferring images from the camera to the processing unit and configured to obtain images of a biopsy sample obtained from the body of the patient. The processing unit is configured to receive image data from an imaging modality capable of obtaining images of internal patient's body parts not directly visible from outside the body, and to display to a user on a display images related to the image data. The processing unit is further configured to generate, from at least one image of a biopsy sample and using the image processing module, a processed image related to the biopsy sample, and to display the processed image on the display.

18 Claims, 7 Drawing Sheets

(51) Int. Cl.
*A61B 8/08* (2006.01)
*A61B 8/12* (2006.01)
*A61B 10/02* (2006.01)
*A61B 8/00* (2006.01)
*A61B 90/13* (2016.01)
*A61B 90/50* (2016.01)
*A61B 5/055* (2006.01)
*A61B 90/00* (2016.01)
*A61B 34/20* (2016.01)
*A61B 34/10* (2016.01)

(52) U.S. Cl.
CPC ...... *A61B 10/0241* (2013.01); *A61B 10/0275* (2013.01); *A61B 90/13* (2016.02); *A61B 90/50* (2016.02); *G06T 7/0014* (2013.01); *A61B 5/055* (2013.01); *A61B 2010/045* (2013.01); *A61B 2034/105* (2016.02); *A61B 2034/107* (2016.02); *A61B 2034/2057* (2016.02); *A61B 2034/2063* (2016.02); *A61B 2034/2065* (2016.02); *A61B 2090/363* (2016.02); *A61B 2090/367* (2016.02); *A61B 2090/374* (2016.02); *A61B 2090/376* (2016.02); *A61B 2090/3782* (2016.02); *A61B 2090/3983* (2016.02); *A61B 2576/00* (2013.01); *G06T 2207/10056* (2013.01); *G06T 2207/30024* (2013.01)

(58) Field of Classification Search
CPC ... A61B 8/0841; A61B 8/4245; A61B 8/4254; A61B 8/4263; A61B 8/5261; A61B 8/5292; A61B 17/3403; A61B 17/3413; A61B 2034/2057; A61B 2034/2063; A61B 2034/2065; A61B 2090/364; A61B 2090/367; A61B 2090/374; A61B 2090/376; A61B 2090/378
See application file for complete search history.

(56) References Cited

U.S. PATENT DOCUMENTS

| | | | |
|---|---|---|---|
| 7,670,333 B2 | 3/2010 | Schatzberger | 606/1 |
| 9,814,442 B2 | 11/2017 | Kruecker et al. | A61B 8/0841 |
| 2003/0135119 A1 | 7/2003 | Lee et al. | 600/461 |
| 2004/0267121 A1 | 12/2004 | Sarvazyan et al. | 600/439 |
| 2008/0072151 A1 | 3/2008 | Song et al. | 715/708 |
| 2008/0081984 A1 | 4/2008 | Lafferty | 600/407 |
| 2009/0048515 A1 | 2/2009 | Suri et al. | 600/443 |
| 2010/0121172 A1 | 5/2010 | Ladic et al. | 600/407 |
| 2011/0040169 A1 | 2/2011 | Kamen et al. | 600/411 |
| 2011/0149340 A1 | 6/2011 | Lipman et al. | 358/1.15 |
| 2012/0206448 A1 | 8/2012 | Embrey | 345/419 |
| 2014/0031718 A1 | 1/2014 | Pastenak et al. | A61B 10/0266 |

FOREIGN PATENT DOCUMENTS

| | | | | |
|---|---|---|---|---|
| EP | 0459535 B1 | 3/2008 | | A61N 5/02 |
| JP | 2000-500031 A | 1/2000 | | A61B 8/00 |
| WO | 2004002319 A2 | 1/2004 | | A61B 17/00 |
| WO | 2004019799 A2 | 3/2004 | | A61B 19/00 |
| WO | 2008063249 A2 | 5/2008 | | A61B 8/00 |
| WO | 200971766 A1 | 6/2009 | | A61B 10/02 |
| WO | 2011161684 A2 | 12/2011 | | A61B 19/00 |
| WO | 2012098483 A1 | 7/2012 | | A61B 10/02 |
| WO | 2013028762 A1 | 2/2013 | | A61B 6/00 |
| WO | 2013015095 A1 | 7/2013 | | G01N 35/10 |
| WO | 2013111133 A1 | 8/2013 | | A61B 10/02 |

SYSTEM AND METHODS FOR PROCESSING A BIOPSY SAMPLE

FIELD OF THE INVENTION

The invention, in some embodiments, relates to the field of biopsy samples, and more particularly, but not exclusively, to systems and methods for obtaining biopsy samples and handling and processing such biopsy samples.

BACKGROUND OF THE INVENTION

Biopsy is a routine procedure used to obtain a sample of a biological tissue from a live organ for a laboratory examination. Often, when carrying out such a procedure, the operating surgeon is assisted by supporting systems. For example, a biopsy sample may be obtained from an internal organ of the body, which is not visible from outside the body and therefore is not directly visible to the surgeon. In such cases an imaging modality such as an ultrasound, MRI or X-ray system may be used to provide to the surgeon images of the region inside the body from which a biopsy sample is to be obtained. Such images, in some cases, may be used to identify sites that are suspected as being abnormal and are therefore candidates for obtaining biopsy samples therefrom. In some cases, such images, particularly if provided to the surgeon continuously in the form of a real-time video stream, may image to the surgeon an organ or a borderline thereof, and may further image the biopsy needle as it is advanced towards a desired biopsy site.

Tracking systems may also be used to provide to the surgeon substantially continuous stream of position data of treatment tools, thereby assisting in navigating a treatment tool to a desired site. Further, position data, provided by such a tracking system, of a portable imaging modality such as an ultrasound portable imaging probe, may be employed to assign image position data to image data obtained by the imaging modality, for example by assigning substantially each pixel in each image a position along a pre-determined coordinate system.

International Patent Application publication number WO/2011/161684 filed Jun. 23, 2011 (designated hereinafter '684), and International Patent Application number PCT/IL2013/050065 filed Jan. 24, 2013 (designated hereinafter '065), both incorporated herein by reference, describe various embodiments of integrated systems incorporating data from a tracking system and from an imaging modality, to facilitate a treatment procedure. Specifically, in some embodiments, such systems may facilitate obtaining a biopsy sample from a desired site in an internal organ, not directly visible from outside the body. According to some embodiments, a series of two dimensional (2D) images of an organ, e.g. a male's prostate, is obtained, and each image is assigned with image position data as described above. A set of substantially parallel images, obtained at sufficiently small spatial intervals between each other, may be suitably arranged and combined to obtain a three-dimensional (3D) image of the imaged organ. Further, by identifying the borderline of the imaged organ, e.g. by methods of computerized image recognition or by human inspection of the images and virtually marking the borderline of the imaged organ, a virtual 3D model of the organ may be generated and stored in a computer's memory.

By continuously tracking the position of a treatment tool, and further by identifying the time of a specific treatment event, a location of a treatment site to which the treatment even is applied, may be recorded in terms of a pre-determined 3D coordinate system, e.g. a pre-determined coordinate system associated with a tracking system. For example, by continuously tracking the position of a biopsy needle, using a tracking system as described above, the position of the needle may be continuously registered relative to the position of a target organ from which a biopsy is to be obtained. By registering the moment of obtaining a biopsy sample, the exact location from which the biopsy sample is obtained may be recorded in terms of the 3D coordinate system. In some embodiments, locations from which biopsy samples were obtained may be thus marked on a virtual 3D model of the organ, and may be used later for navigating a treatment tool to the same sites.

SUMMARY OF THE INVENTION

Aspects of the invention, in some embodiments thereof, relate to systems and methods for obtaining biopsy samples and handling and processing such biopsy samples. More specifically, aspects of the invention, in some embodiments thereof, relate to systems and methods for imaging an obtained biopsy sample.

As discussed above, current systems, specifically such that include an imaging modality and/or a tracking system, may assist a surgeon during a treatment procedure in navigating a treatment tool towards a treatment site not directly visible to the surgeon. Such assistance may be provided using one or more techniques. For example by presenting to the surgeon, substantially in real time, the location of a treatment tool and a target location to be treated, relative to a same reference frame (e.g. a same 3D coordinate system) provides the surgeon a feedback on the relative distance and direction between the treatment tool and the treatment site, thereby assisting the surgeon to navigate the treatment tool towards the desired treatment site. As another example, the treatment tool, or a synthetic mark indicating the location of the treatment tool, may be displayed on a screen in real time together with an image of the organ to be treated or a virtual 3D model of the organ, positioned on the screen in accordance with the real 3D position of the organ in the body as this position is revealed e.g. from images of the organ. By displaying on a same screen the real-time location of the treatment tool and the treatment site, the surgeon is provided with a feedback on the relative distance and direction between the treatment tool and the treatment site.

Enhancing the real-time feedback provided to a surgeon during operation can further simplify the operation and enhance its quality. Specifically, providing the surgeon with an image of an obtained biopsy sample can significantly improve the surgeon decisions regarding the location from which the next sample will be obtained and regarding the number of samples that are still to be obtained from the organ during the immediate biopsy session. For example, an image of an obtained biopsy sample may indicate to the surgeon that the sample is truncated, fragmented or broken, leading to a decision to obtain a next sample from substantially the same site to avoid reducing detection probability. Further, an image of a biopsy sample can be stored in the computer memory for later use or inspection. Further yet, by employing image processing and image recognition techniques to the image of a biopsy sample, spatial characteristics—for example a length of the sample—may be obtained automatically.

While employing a system capable of presenting to the surgeon, in real time and during a biopsy session, a virtual 3D model of an inspected organ, and further capable of adding to the model a synthetic mark indicating the location from which a biopsy sample was obtained, the actual length of the imaged sample may be graphically displayed, by displaying a synthetic mark the length of which is proportional to the length of the imaged sample. Moreover, by imaging the biopsy sample on the biopsy needle, the exact location of the sample on the biopsy needle may be measured. For example, the location of the sample on the notch of the biopsy needle may be detected or the distance of the sample from a landmark of the biopsy needle, such as the distal tip, may be measured. Such measurement of the distance may be accomplished e.g. automatically using image recognition techniques, or manually, by a user, or by any combination thereof.

When employing a system incorporating an imaging modality and/or a tracking system as described above, and further when the instant position of a biopsy needle is registered in terms of a 3D coordinate system at the moment of obtaining the biopsy sample, the exact location of the site from which the sample was obtained may be registered. This exact location may then be displayed for the surgeon in real time for example on a virtual 3D model of the organ, so that the surgeon may decide on the position, in the inspected organ, from which a next biopsy sample should be obtained. Such exact location may further be stored for later use, for example to be displayed on a virtual 3D model of the organ during a next treatment session, when the surgeon considers obtaining more biopsy samples or when the surgeon considers employing a local and focused treatment to a particular treatment site.

Thus, according to an aspect of some embodiments, there is provided a system for facilitating obtaining a biopsy sample from a body of a patient, comprising a display for displaying images to a user. The system further comprises a processing unit functionally associated with the display, wherein the processing unit comprises an image processing module. The system further comprises a camera functionally associated with the processing unit for transferring images from the camera to the processing unit and configured to obtain images of a biopsy sample obtained from the body of the patient. The processing unit is configured to receive image data from an imaging modality capable of obtaining images of internal patient's body parts not directly visible from outside the body, and to display to a user on the display images related to the image data. The processing unit is further configured to generate, from at least one image of a biopsy sample and using the image processing module, a processed image related to the biopsy sample, and to display the processed image on the display.

According to some embodiments, the imaging modality comprises an ultrasonography module, capable of obtaining ultrasound images of internal body parts. According to some embodiments, the imaging modality comprises a magnetic resonance imaging (MRI) module, capable of obtaining MRI images of internal body parts. According to some embodiments, the imaging modality comprises an X-ray imaging module capable of obtaining X-ray images of internal body parts.

According to some embodiments, the image processing module is configured to generate a map of the biopsy sample from an image of the biopsy sample received from the camera. According to some embodiments, the image processing module is configured to identify a border of the biopsy sample on an image of a biopsy sample received from the camera. According to some embodiments, the image processing module is configured to generate from an image of a biopsy sample a contour substantially outlining the border of the biopsy sample on the image. According to some embodiments, the image processing module is configured to generate from an image of a biopsy sample broken to pieces, a multitude of separate contours wherein each such contour substantially outlines the border of one piece of the biopsy sample on the image.

Current methods for handling and processing biopsy samples may include a step of verifying the source of the biopsy sample to avoid errors while reporting results of laboratory tests. An example of a verification method comprises identifying the DNA or DNA-related hereditary material in the sample, and comparing the DNA profile associated with the sample to the DNA profile of the person from which the sample is believed to have been taken. For example, a sample may be obtained from the biopsy sample soon before or soon after a pathological inspection, e.g. under a microscope, and the sample is taken to DNA profiling. Only if the DNA associated with the sample is found identical to the DNA of the person from which the sample is believed to have been taken, pathology test results are reported to that person.

DNA profiling is an expensive test, requiring substantial resources of equipment, trained personnel and time. There is thus a need for a method that facilitates verification of the source of the biopsy sample over methods of the prior art, by validating or disproving the identity of the biopsy sample using simpler methods.

By employing imaging of a biopsy sample obtained from a body of a patient as described herein, verifying the source of the biopsy sample may be accomplished. There is thus provided a method of processing a biopsy sample, comprising: providing a biopsy sample obtained from a body of a patient; obtaining a first image of the biopsy sample; obtaining a second image of the biopsy sample, and comparing image data obtained from the first image to image data obtained from the second image, thereby validating or disproving the identity of the biopsy sample.

According to some embodiments, the method further includes a step of chemically treating the biopsy sample, performed after obtaining the first image and before obtaining the second image. According to some embodiments, the method further includes a step of sectioning the biopsy sample performed after obtaining the first image and before obtaining the second image. According to some embodiments, obtaining at least one of the first image and the second image is carried out using an imaging device. According to some embodiments the imaging device is a camera. According to some embodiments the method further includes a step of dyeing the biopsy sample prior to performing the step of obtaining a first image of the biopsy sample.

According to some embodiments, the method further includes processing the first image and the second image to generate a map from the image data of each image, wherein the comparing step includes comparing the map obtained from the first image to the map obtained from the second image. According to some embodiments, the maps represent topographic variations of the biopsy samples. According to some embodiments, the maps represent material variations of the biopsy samples.

This invention separately provides a system which can be used for displaying a processed image of a biopsy sample, soon after obtaining the biopsy sample from a body.

This invention separately provides a system which can be used for displaying a map of a biopsy sample, the map representing topographic variations and/or material variations of the sample.

This invention separately provides a system which can be used for providing spatial dimensions of a biopsy sample, extracted from an image of the sample.

This invention separately provides a system which can be used for displaying a combined image comprising a processed image of a biopsy sample, and an image of an internal body part, not visible from outside the body.

This invention separately provides a system which can be used for displaying a combined image comprising an image of an internal body part, not visible from outside the body, or a virtual model of such internal body part, and a processed image of a biopsy sample, or a synthetic mark representing such biopsy sample, located, on the combined image, at a location corresponding to the location in the internal body part from where the biopsy sample was obtained.

This invention separately provides a method which can be used for obtaining biopsy samples from a desired location in an internal body part, not directly visible from outside the body.

This invention separately provides a method which can be used for validating or disproving an identity of a biopsy sample prior to sending an examination result concerning the sample to the person from whom the sample is believed to have been taken.

Certain embodiments of the present invention may include some, all, or none of the above advantages. Further advantages may be readily apparent to those skilled in the art from the figures, descriptions, and claims included herein. Aspects and embodiments of the invention are further described in the specification hereinbelow and in the appended claims.

Unless otherwise defined, all technical and scientific terms used herein have the same meaning as commonly understood by one of ordinary skill in the art to which this invention pertains. In case of conflict, the patent specification, including definitions, governs. As used herein, the indefinite articles "a" and "an" mean "at least one" or "one or more" unless the context clearly dictates otherwise.

Embodiments of methods and/or devices of the invention may involve performing or completing selected tasks manually, automatically, or a combination thereof. Some embodiments of the invention are implemented with the use of components that comprise hardware, software, firmware or combinations thereof. In some embodiments, some components are general-purpose components such as general purpose computers or oscilloscopes. In some embodiments, some components are dedicated or custom components such as circuits, integrated circuits or software.

For example, in some embodiments, some of an embodiment may be implemented as a plurality of software instructions executed by a processor, for example which is part of a general-purpose or custom computer. In some embodiments, the processor or computer comprises volatile memory for storing instructions and/or data and/or a non-volatile storage, for example, a magnetic hard-disk and/or removable media, for storing instructions and/or data. In some embodiments, implementation includes a network connection. In some embodiments, implementation includes a user interface, generally comprising one or more of input devices (e.g., allowing input of commands and/or parameters) and output devices (e.g., allowing reporting parameters of operation and results).

Aspects and embodiments of the invention are described in the specification hereinbelow and in the appended claims.

BRIEF DESCRIPTION OF THE FIGURES

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

In the Figures.

DESCRIPTION OF SOME EMBODIMENTS OF THE INVENTION

The principles, uses and implementations of the teachings herein may be better understood with reference to the accompanying description and figures. Upon perusal of the description and figures present herein, one skilled in the art is able to implement the invention without undue effort or experimentation.

Figure 1:
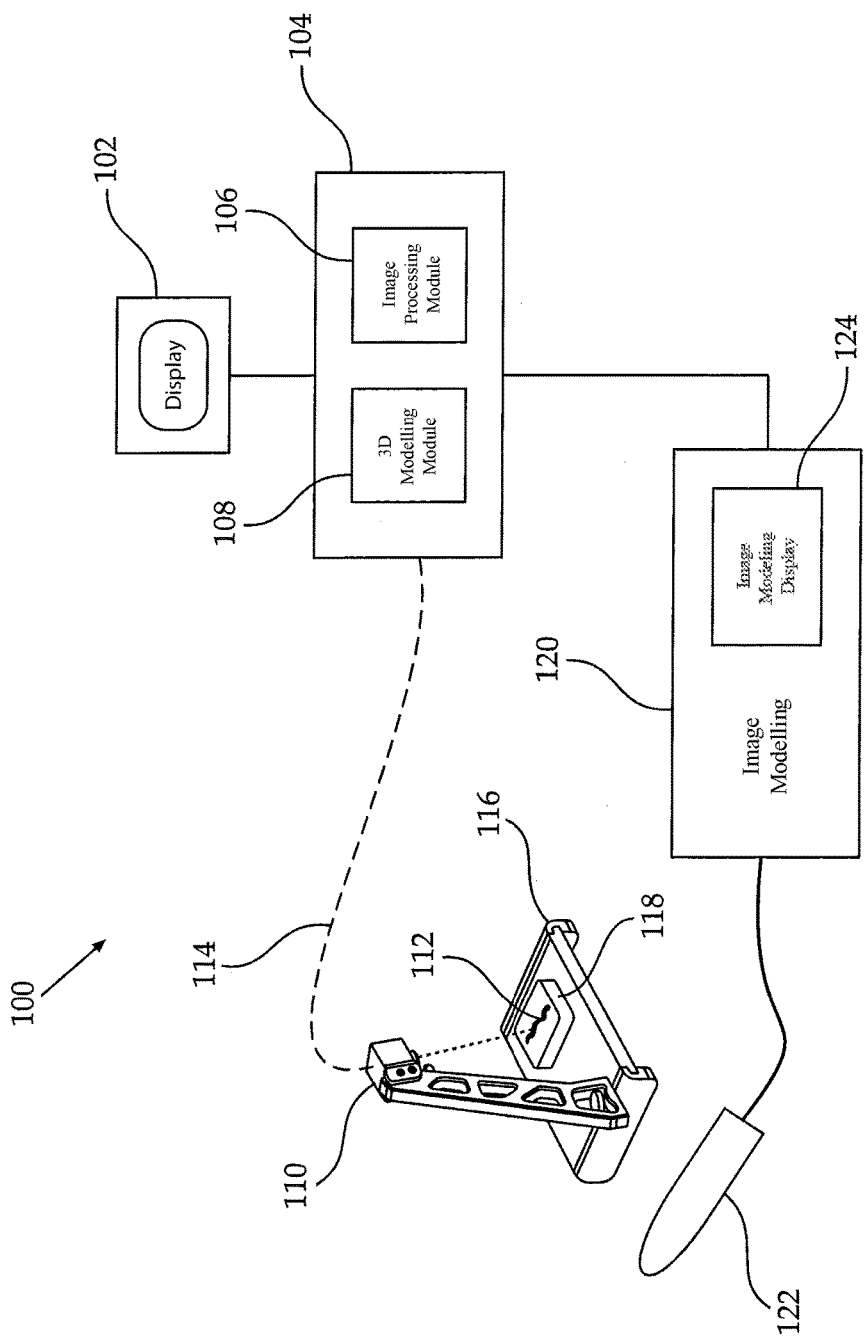
FIG. 1 schematically depicts an embodiment of a system for facilitating obtaining a biopsy sample from a body of a patient.

FIG. 1 schematically depicts an embodiment of a system 100 for facilitating obtaining a biopsy sample from a body of a patient. System 100 comprises a display 102 for displaying images to a user. System 100 further comprises a processing unit 104, functionally associated with display 102 and comprising an image processing module 106. System 100 further comprises a camera 110 functionally associated with processing unit 104 for transferring images from the camera to the processing unit. Camera 110 is configured to obtain images of a biopsy sample 112 obtained from the body of a patient and to transfer such images, via a communication channel 114, to processing unit 104. Transferring the images from the camera to the processing unit may be done automatically, in real time, meaning that every image is transferred to processing unit 104 substantially immediately after the image is obtained. Or images may be stored in a memory device in the camera and transferred to processing unit 104 upon the occurrence of a pre-determined event. Such a pre-determined event may be a command by an operator or any decision criterion programmed e.g. to the camera, such as obtaining a pre-determined number of images, attaining of which may trigger transferring the images. According to some embodiments communication channel 114 may comprise electric wires. According to some embodiments communication channel 114 may be wireless, e.g. employing radio communication.

System 100 is configured to functionally associate with an imaging modality 120, capable of obtaining images of internal patient's body parts not directly visible from outside the body. Examples of imaging modality 120 may be an ultrasound imaging system, an MRI imaging system or an X-ray imaging system. Imaging modality 120 may comprise a portable imaging probe 122 such as an ultrasound portable imaging probe in an ultrasound imaging system. Imaging modality 120 may further comprise an imaging modality display 124 for displaying e.g. obtained images of internal body parts.

Processing unit 104 is configured to receive image data from imaging modality 120 and to display to a user on display 102 images related to the image data. For example, processing unit 104 is capable of receiving ultrasound images from imaging modality 120, imaging modality 120 being and ultrasonography system, and displaying the images on display 102. In some embodiments processing unit 104 may manipulate the image data stream received from imaging modality 120 and display images after such manipulation on display 102. Such manipulation may comprises freezing an image, zooming in and out relative to an area on the image selected by a user, or adding text or synthetic marks to the related images displayed on display 102.

By employing image processing module 106, processing unit 104 is configured to generate a processed image related to biopsy sample 112 from at least one image of biopsy sample 112, and to display the processed image on display 102.

Figure 2A:
FIG. 2A schematically depicts an image obtained by the camera of FIG. 1, of a biopsy sample.
Figure 2B:
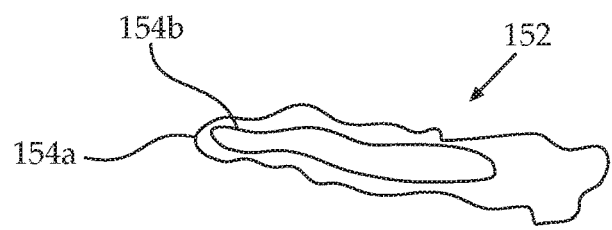
FIG. 2B schematically depicts a map generated by the image processing module of FIG. 1, representing topographic variations of the biopsy sample imaged in FIG. 2A.

FIG. 2A schematically depicts an image 150*a* of a biopsy sample obtained by camera 110 and transferred to processing unit 104 for image processing by image processing module 106. Image processing module 106 is configured to generate a map of the biopsy sample from image 150*a*. FIG. 2B schematically depicts a map 152 generated by image processing module 106 according to some embodiments, representing topographic variations of the imaged biopsy sample. Specifically, contours 154*a* and 154*b* represent height variations of the sample above the surface wherein contour 154*a* outlines the border of the biopsy sample on image 150*a*. Identifying the border of the sample in image 150*a* may be accomplished automatically by image processing module 106, employing methods of object recognition well known in the art, or such identification may be assisted by a mark or a multitude of marks virtually marked by a user on image 150*a* (e.g. a multitude of points marked by the user along the border of the sample in image 150*a*).

Figure 2C:
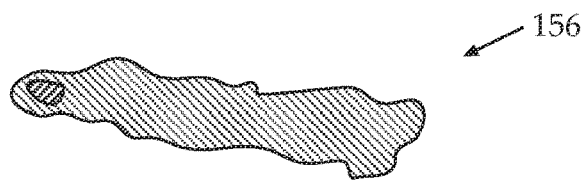
FIG. 2C schematically depicts a map generated by the image processing module of FIG. 1, representing material variations of a the biopsy sample imaged in FIG. 2A.

FIG. 2C schematically depicts a map 156 generated by image processing module 106 according to some embodiments, representing material variations of the biopsy sample imaged in image 150*a*. Identifying material variations may be accomplished for example by identifying regions in image 150*a* having different colors or different grey levels.

Figure 2D:
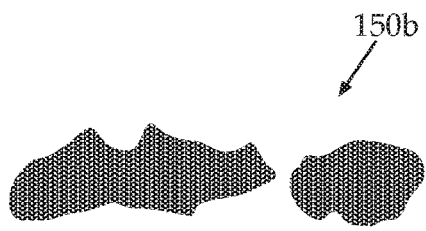
FIG. 2D schematically depicts an image of a biopsy sample broken to two pieces.
Figure 2E:
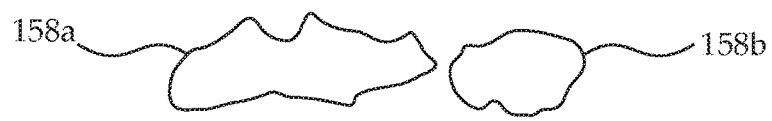
FIG. 2E schematically depicts a map generated by the image processing module of FIG. 1, of the biopsy sample imaged in the image of FIG. 2D.

FIG. 2D schematically depicts an image 150*b* of a biopsy sample broken to two pieces. Each of two contours 158*a* and 158*b*, respectively, generated by image processing module 106 according to some embodiments, substantially outlines the border of one piece of the biopsy sample on the image 150*b*.

According to some embodiments, communication channel 114 may comprise electric wires for transferring images from the camera to the processing unit. According to some embodiments, communication channel 114 may comprise a wireless communication channel with the processing unit for transferring images from the camera to the processing unit. According to some embodiments, camera 110 is electrically associated with a radio transmitter (not shown) which may be, for example, attached to the camera or positioned proximal to the camera, whereas processing unit 104 is functionally associated with a radio receiver which may be, for example, positioned proximal thereto. Image data obtained by camera 110 may thus be electrically transferred to the radio transmitter, then transmitted from the radio transmitter and received by the radio receiver, and electrically transferred to processing unit 104.

According to some embodiments, communication channel 114 is uni-directional, being configured to transfer images from the camera to the processing unit. According to some embodiments, communication channel 114 may be bi-directional. According to some embodiments, camera 110 is configured and functionally associated with processing unit 104 for receiving operational commands from processing unit 104. Thus, a user operating system 100 may activate camera 110 through a user interface (not shown in FIG. 1) of system 100, transferring commands through communication channel 114. Such a user interface may comprise typical user interface devices for interfacing with a computerized system such as a keyboard, a mouse, a joy stick etc. as is well known in the art, and/or a dedicated user interface such as an electronic command panel comprising control buttons and signaling components such as lights and screens. According to some embodiments, camera 110 may be stills camera, providing a single image or a series of distinct images upon activation. According to some embodiments, camera 110 may be a video camera, providing a video stream upon activation.

Figure 3A:
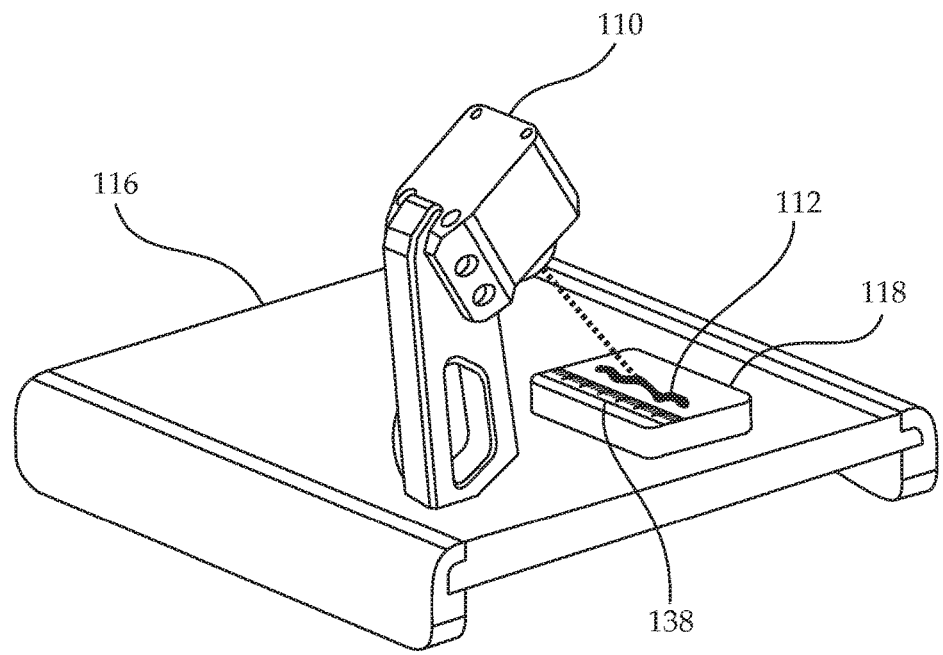
FIG. 3A schematically depicts an embodiment of the camera of FIG. 1 attached to a stand, wherein the stand is configured to support a biopsy sample so that the camera is aimed to the biopsy sample to obtain an image thereof.
Figure 3B:
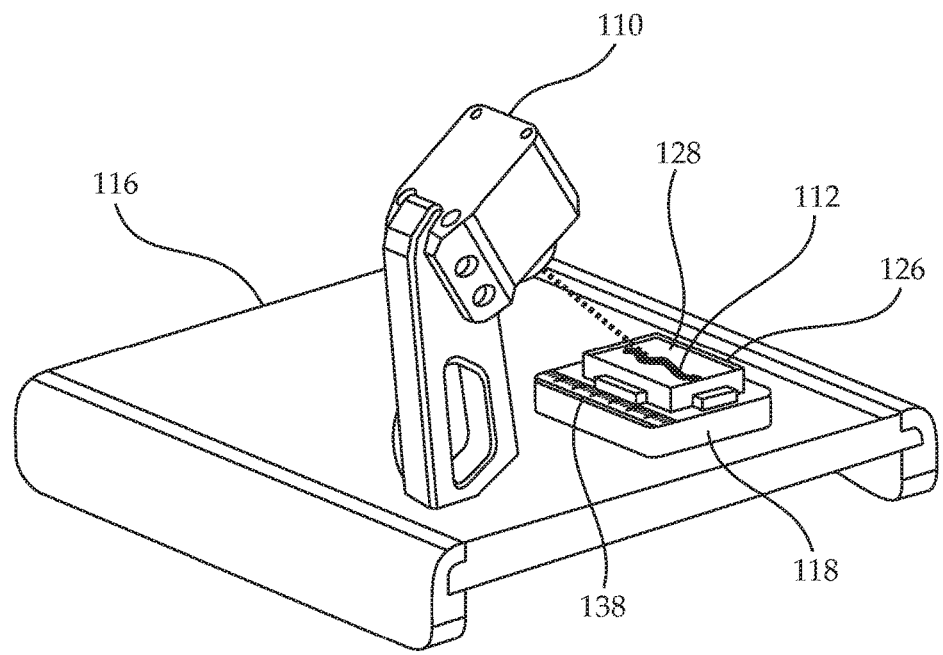
FIG. 3B schematically depicts an embodiment of the camera of FIG. 1 attached to a stand, wherein the stand is configured to support a sample holder carrying a biopsy sample so that the camera is aimed to the biopsy sample to obtain an image thereof.
Figure 3C:
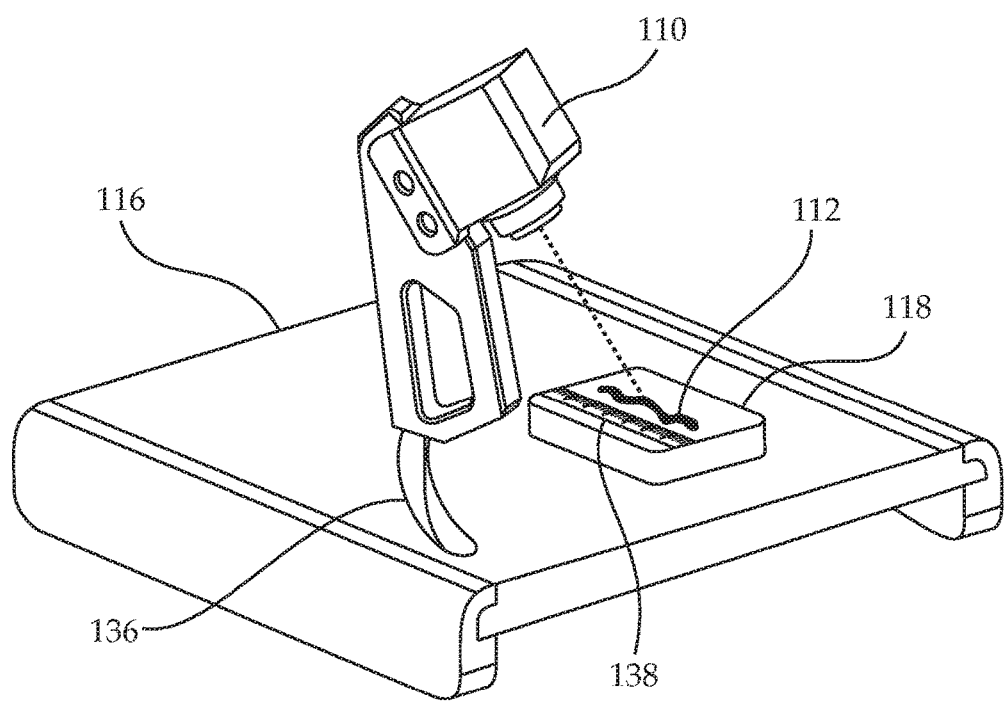
FIG. 3C schematically depicts the embodiment shown in FIG. 3A wherein the camera is aiming at the biopsy sample from a different direction.

FIGS. 3A and 3B schematically depict camera 110 attached to stand 116, wherein stand 116 is configured to support biopsy sample 112 so that camera 110 is aimed to the biopsy sample to obtain an image thereof. Stand 116 comprises a pedestal 118 configured and aligned to support biopsy sample 112 thereon. According to some embodiments pedestal 118 may be coated on a top surface thereof with a non-adhesive material such as polypropylene or polytetrafluoroethylene so that the biopsy sample 112 does not adhere to pedestal 118. After obtaining an image of the biopsy sample by camera 110, biopsy sample 112 may be easily removed from pedestal 118.

According to some embodiments pedestal 118 may be configured for installment of a sample holder such as cassette 126 thereon, as is schematically depicted in FIG. 3B. Cassette 126 may be configured to hold and/or to carry a biopsy sample thereon and an image of a biopsy sample may be obtained by installing cassette 126 carrying a biopsy sample thereon on pedestal 118 as depicted in FIG. 3B, followed by activating camera 110. According to some embodiments cassette 126 may comprise an adhering surface 128 configured to adhere to a biological sample upon contacting such a biological sample. Some embodiments of a sample holder such as e.g. cassette 126 are described in detail in International Patent Application publication number WO2013105095 filed on Jan. 10, 2013 (herein '095), which is incorporated by reference herein in its entirety.

According to some embodiments stand 116 may comprise a groove 136 and camera 110 is attached to stand 116 on groove 136. Camera 110 may be fixedly attached to stand 116 at a desired point along groove 136 thereby aiming to biopsy sample 112 from several directions and obtaining images of biopsy sample 112 from several angles.

According to some embodiments, image processing module 106 is configured to employ methods known in the art to generate a virtual 3D model of biopsy sample 112 by processing several images of the biopsy sample obtained from several directions, respectively.

According to some embodiments a length scale 138 is positioned on pedestal 118 or proximal to pedestal 118, thereby allowing an image of the biopsy sample to incorporate a length scale. By comparing, on the image, the biopsy sample and the length scale, dimensions of the biopsy sample, such as length or width, may be obtained. According to some methods, dimensions of the biopsy sample may be obtained manually by comparing the dimensions of the image of the biopsy sample within its borders to the length scale, e.g. using a ruler. According to some embodiments dimensions of the biopsy sample may be obtained automatically using image processing and object recognition techniques, by image processing module 106. For example, the maximum distance, measured in pixels, between points on a contour of a map of the biopsy sample such as contour 154*b* in FIG. 2B, may be compared to a distance, measured in pixels, along the image of length scale 138. Other methods and techniques, as is well known in the art, of establishing dimensions of the biopsy sample imaged besides length scale 138, are contemplated.

According to some embodiments processing unit 104 further comprises a 3D modelling module 108. 3D modelling module 108 is configured to receive image data provided by imaging modality 120, wherein the image data is assigned with corresponding image position data along pre-selected coordinates. Image data assigned with image position data means that substantially every pixel in an image corresponding to the image data is assigned with a location value along a pre-determined set of coordinates. Image data so assigned with image position data may be received for example from an MRI imaging system wherein an image typically corresponds to a well-defined plane in space. As another example, image data assigned with image position data may be received from an ultrasound system having an portable imaging probe with known position. When the position of the portable imaging probe is known, the position corresponding to the images obtained by the portable imaging probe may also be know, and image position data may thus be assigned to such images. 3D modelling module 108 is further configured to create a virtual 3D model of an organ, using suitably selected image data, assigned with image position data, of the organ as is explained in detail for example in '684 and in '065.

Figure 4:
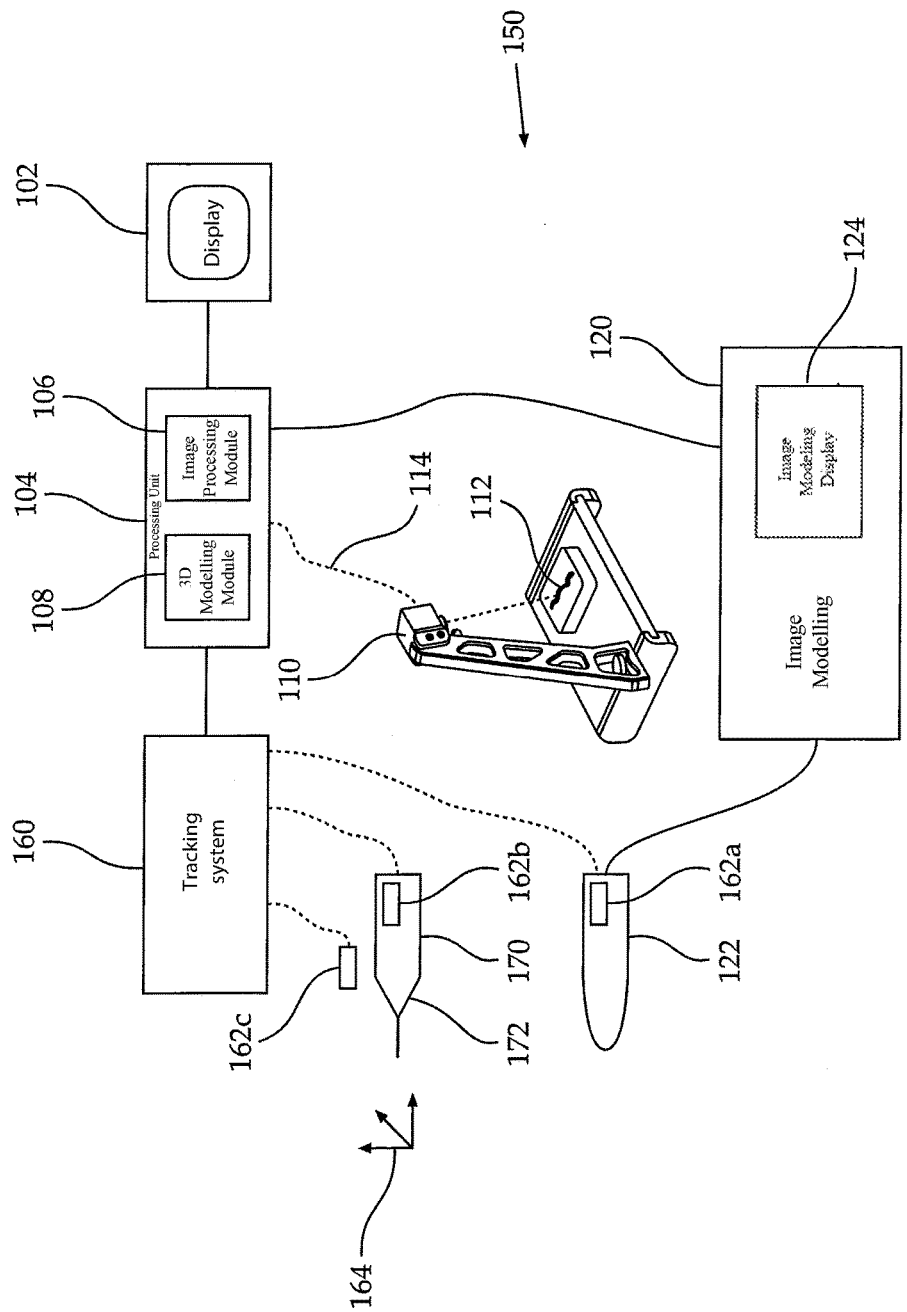
FIG. 4 schematically depicts an embodiment of a system for facilitating obtaining a biopsy sample from a body of a patient comprising the system of FIG. 1 and further comprising a tracking system according to the teachings herein.

FIG. 4 schematically depicts an embodiment of a system 140 comprising system 100 described above for facilitating obtaining a biopsy sample from a body of a patient, and further comprising a tracking system 160. Tracking system 160 is functionally associated with one or more tracking sensors 162, for example tracking sensors 162*a*, 162*b* and 162*c*. According to some embodiments each tracking sensor 162 is configured to report to tracking system 160 the position thereof relative to a fixed point in space, and tracking system 160 is configured to calculate and provide the location and orientation of each tracking sensor 162, along a pre-selected coordinate system 164, substantially in real time. Tracking a position of a tracking sensor 162 by tracking system 160 may employ one of several known methods and techniques, or a combination thereof. For example, according to some embodiments each tracking sensor may be mechanically connected to a fixed point in space by a folding arm comprising rigid segments interconnected by joints. Sensors measuring folding angles of the joint may be employed to report a location in space of a tracking sensor relative to the point in space to which it is mechanically connected. According to some embodiments each tracking sensor may be equipped with accelerometers, whereas the tracking sensor may be configured to report e.g. magnitude and direction of a displacement thereof by integrating acceleration values measured by the accelerometers. According to some embodiments, tracking system 160 comprises an electromagnetic field generating device (not shown) generating an electromagnetic (EM) field having a known magnitude and direction in substantially every point in a working space. Each tracking sensor 162 may be configured to detect and report, substantially instantaneously, the magnitude and direction of the EM field, substantially at the position of the tracking sensor 162, and tracking system 160 is configured to receive such reports from each tracking sensor and to translate such reports into a position data along a 3D coordinate system. An example of a commercially available EM tracking system is 3D Guidance trakSTAR™ by Ascension Technology Corporation.

Tracking system 160 in FIG. 4 is functionally associated with processing unit 104 and configured to provide to processing unit 104 position data comprising location and orientation of tracking sensors 162 along coordinate system 164 substantially in real time. Tracking sensor 162*a* is fixedly attached to portable imaging probe 122 of imaging modality 120, thereby having a known spatial relation with portable imaging probe 122. Processing unit 104 is configured to receive position of tracking sensor 162*a* reported by tracking system 160 to processing unit 104, and thereby to register the position of portable imaging probe 122. According to some embodiments imaging modality 120 comprises an ultrasound imaging system, and portable imaging probe 122 comprises an ultrasound portable imaging probe, for example a trans-rectal ultrasound probe. Portable imaging probe 122 obtains images from regions in space, e.g. planes, having known spatial relation with the position of portable imaging probe 122. By considering the position of portable imaging probe 122 reported by tracking system 160 and the known spatial relation between portable imaging probe 122 and the regions in space from which image data is obtained by the portable imaging probe, processing unit 104 may assign image position data received from the tracking system 160, to image data received from the imaging modality 120.

According to some embodiments, a tracking sensor 162*b* may be fixedly attached to a portable treatment tool 170.

Processing unit 104 is configured to receive position of tracking sensor 162b reported by tracking system 160 to processing unit 104, and thereby to register the position of portable treatment tool 170 substantially continuously, substantially in real-time.

According to some embodiments treatment tool 170 may comprise a biopsy needle 172. According to some embodiments, biopsy needle 172 may be configured to obtain a biopsy sample of e.g. the prostate.

According to some embodiments, portable imaging probe 122 may comprise a needle guide (not shown) for guiding a portable treatment tool 170 such as biopsy needle 172 along a pre-defined trajectory in the course of a treatment. For example, portable imaging probe 122 may comprise a transrectal ultrasound probe having a needle guide suitable for insertion of treatment tools, e.g. for insertion of a biopsy needle configured to obtain biopsy samples from the prostate. When biopsy needle 172 is suitably placed in the needle guide of portable imaging probe 122, biopsy needle 172 has partially known spatial relation with tracking sensor 162a. According to some embodiments, processing unit 104 is configured to generate a combined image comprising image data received from imaging modality 120 and a synthetic mark indicating a location of biopsy needle 172. The synthetic mark is displayed in the combined image in a location corresponding to the position of biopsy needle 172 as reported by tracking sensor 162a or tracking sensor 162b, relative to the region in space from which the image data is collected, as reported by tracking sensor 162 fixed to imaging probe 122. For example, a synthetic mark may include a line extending across an ultrasound image, the line corresponding to the direction of the needle guide in the plane of the ultrasound image. When treatment tool 170 (e.g. biopsy needle 172) is in the needle guide the position thereof on the ultrasound image is partially known, being known to be along the line, whereas the location of the needle (e.g. the tip of the needle) along the line is unknown. Using position data of tracking sensor 162a, processing unit 104 may assign the ultrasound images image position data, thereby assigning each pixel in the image a position data along the coordinate system 164. The whereabouts of treatment tool 170 is partially known, that is to say known to be restricted to the position coordinates of the line.

According to some embodiments processing unit 104 comprises 3D modelling module 108. As described above, image data obtained by imaging modality 120 employing portable imaging probe 122 is assigned image position data by processing unit 104 according to position data reported by tracking sensor 162a. 3D modelling module 108 is configured to receive such image data assigned with corresponding image position data as is described in detail also in '684 and '065. According to some embodiments, 3D modeling module 108 is configured to combine image data of a series of 2D images and into a 3D image comprising "volume pixels" ("voxels"). For example, a series of substantially parallel 2D images obtained at small intervals from one another, may be combined, according to the image position data assigned to them, to generate a single 3D image encompassing the volume imaged by the series of the 2D images.

According to some embodiments 3D modelling module 108 is configured to create a virtual 3D model of an organ using suitably selected image data, assigned with image position data, of the organ. According to some embodiments processing unit 104 is configured to generate a combined image comprising a virtual 3D model of an organ generated by 3D modelling module 108, and a synthetic mark indicating a location of biopsy needle 172. According to some embodiments the location of the synthetic mark on the combined image relative to the virtual 3D model is dependent on a position reported by tracking system 160 and received by processing unit 104.

Figure 5:
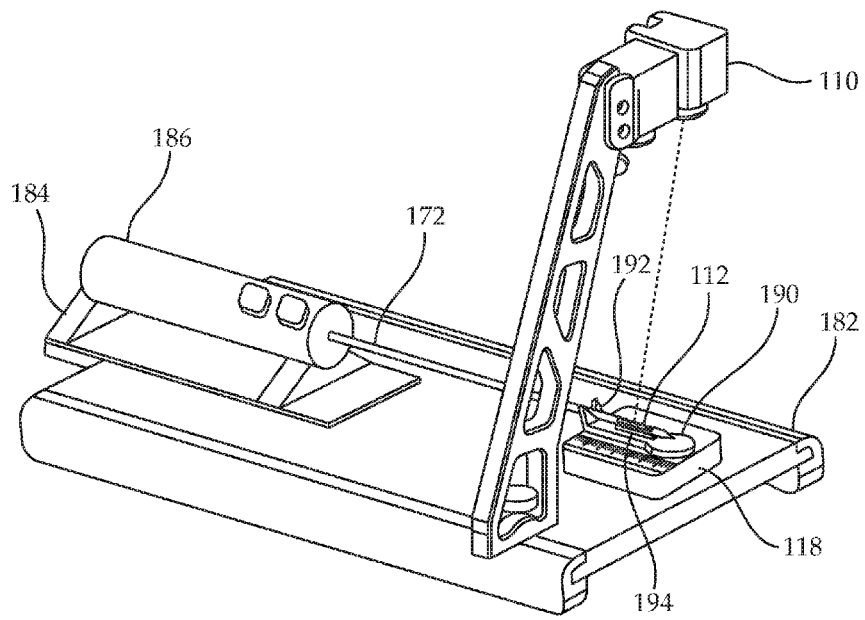
FIG. 5 depicts schematically an embodiment of the camera of FIG. 1 or FIG. 4 configured to obtain an image of biopsy sample supported on a biopsy needle.

According to some embodiments image processing module 106 is configured to generate from an image of a biopsy sample 112 received from camera 110 a contour substantially outlining the border of biopsy sample on the image, as described above. FIG. 5 depicts schematically an embodiments of a camera 110 configured to obtain an image of biopsy sample 112 supported on a biopsy needle 172. A stand 182 comprises a gun house 184 configured to secure therein a biopsy gun 186 comprising biopsy needle 172. A pedestal 118 supports the distal end of the biopsy needle in a horizontal alignment. Pedestal 118 supports a needle bed 190 having two alignment shoulders 192 and a support platform 194, aligned along the center line of needle bed 190. Thus needle bed 190 may support biopsy needle 172 so that biopsy needle 172 is disposed between alignment shoulders 192 so that the notch of the biopsy needle is supported on support platform 194. Stand 182 further comprises a length scale 138 arranged on pedestal 118 proximal support platform 194 and extending along biopsy needle 172. Camera 110 is positioned so as to aim to biopsy sample 112 supported on the notch of the biopsy needle thereby camera 110 is being configured to obtain an image of the biopsy sample supported in biopsy needle 172.

Figure 6A:
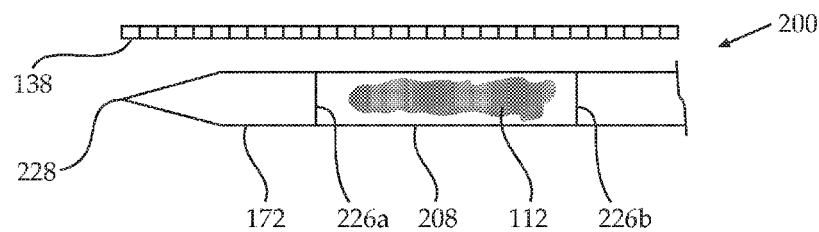
FIG. 6A depicts schematically an image obtained by the camera of FIG. 1 or FIG. 4, of a biopsy sample supported on a notch of a biopsy needle.

FIG. 6A depicts schematically an image 200 obtained by camera 110 (not shown in this Figure) of biopsy sample 112 supported on a notch 208 of biopsy needle 172. Length scale 138 positioned proximal to the biopsy needle and the biopsy sample, provides a length scale to the imaged items in image 200.

Figure 6B:
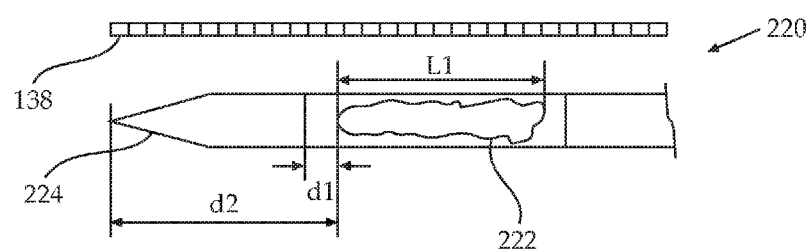
FIG. 6B depicts schematically a map generated from the image of FIG. 6A by an embodiment of the image processing module of FIG. 1 or FIG. 4, and FIG. 7 schematically depicts an embodiment of a method of processing a biopsy sample, according to the teachings herein.

FIG. 6B depicts schematically a map 220 generated by image processing module 106 from image 200 of FIG. 6A. Map 220 comprises a contour 222 outlining the border of biopsy sample 112 in image 200, and a contour 224 outlining the border of the distal portion of biopsy needle 172. By employing known methods of image recognition and known methods of measurement of critical dimensions, processing unit 104 is configured to determine a desired dimension such as L1 of contour 222. By comparing L1 (e.g. in terms of number of pixels) to a length unit on length scale 138, a length of biopsy sample 112 is determined. Likewise, processing unit 104 is configured to determine, from map 220 of contours 222 and 224, a distance between a landmark of biopsy sample 112 to a landmark of biopsy needle 172. For example, processing unit 104 is configured to determine a distance d1 between the most distal end of contour 222 and the distal end 226a of the notch 208 of biopsy needle 172 or the distance d2 between the most distal end of contour 222 and the distal tip 228 of biopsy needle 172. Methods of image recognition and measurement of critical dimensions are well known e.g. in the art of automatic and computerized inspection and quality control of manufacturing of Printed Circuit Boards and manufacturing of microelectronics such as VLSI devices on silicon wafers.

By considering the position of biopsy needle 172 along coordinate system 164 at a moment when a biopsy sample is obtained, provided e.g. by tracking system 160, and considering the length of obtained biopsy sample 112 and position thereof relative to biopsy needle 172, according the method described above, processing unit 104 may calculate the position and dimension of the site from which biopsy sample 112 was obtained, along coordinate system 164. Processing unit 104 is thereby further configured to generate a combined image comprising a virtual 3D model of an organ, or a 3D image of the organ (composed of voxels as described above), generated by 3D modelling module 108, and a synthetic mark indicating a position (location and orientation) in the organ from which the biopsy sample was obtained. According to some embodiments processing unit 104 is configured to generate a combined image comprising a virtual 3D model of an organ or a 3D image of the organ generated by 3D modelling module 108, and a scaled image of biopsy sample 112 positioned in the combined image so as to indicate a location in the organ from which biopsy sample 112 was obtained. A scaled image means that the actual image of biopsy sample 112, obtained e.g. from image 200, is scaled to have the same scale (ratio of number of pixels to a length unit) of the virtual 3D model of the organ or the 3D image of the organ.

As discussed above, current methods for handling and processing biopsy samples during preparation prior to laboratory tests (e.g. inspection under a microscope) and including such tests, may include a step of verifying the source of the biopsy sample to avoid errors while reporting results of the laboratory tests. Some current methods of such verification are based on DNA profiling and are therefore less than optimal, being relatively expensive and intense in consuming resources such as equipment, trained personnel and time. There is thus a need for a method that facilitates verification of the source of the biopsy sample over methods of the prior art, by validating or disproving the identity of the biopsy sample using simpler methods.

Figure 7:
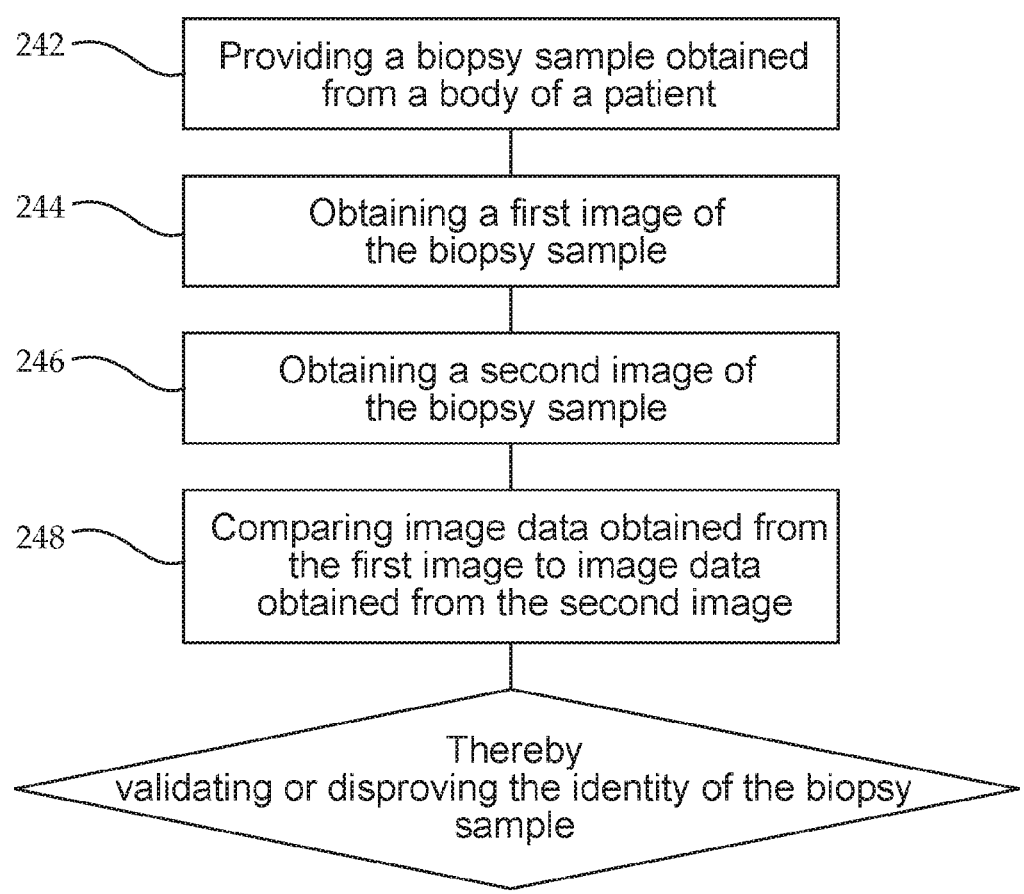

By employing imaging of a biopsy sample obtained from a body of a patient as described herein, verifying the source of the biopsy sample may be accomplished. FIG. 7 schematically depicts a method of processing a biopsy sample. The method includes step 242 of providing a biopsy sample obtained from a body of a patient. The method further includes step 244 of obtaining a first image of the biopsy sample. The method further includes step 246 of obtaining a second image of the biopsy sample. The method further includes step 248 of comparing image data obtained from the first image to image data obtained from the second image, thereby validating or disproving the identity of the biopsy sample.

According to some embodiments, the method of FIG. 7 may be carried out as described below: a biopsy sample is obtained from a patient using a known method, e.g. using a biopsy obtaining tool such as a scalpel or a biopsy needle. Soon after obtaining the biopsy sample, a first image of the sample is obtained by a first camera. The first image may be obtained while the biopsy sample is supported on a sample holder or on any suitable surface under the first camera, as schematically depicted in FIGS. 3A and 3B. Alternatively or additionally, the first image may be obtained when the biopsy sample is supported on the tool that was used to obtain the sample (provided that the biopsy sample may be visibly exposed on the tool), as schematically depicted in FIG. 5 above.

According to some embodiments a tissue handling device may be used to transfer the biopsy sample from a tool that was used to obtain the sample (e.g. a scalpel or a biopsy needle) onto a sample holder such as a cassette, while maintaining an orientation of the sample. In other words, the shape of the sample on e.g. the scalpel is maintained on the sample holder. For example, '095 discloses a device for collecting onto a sample holder a biological tissue carried on a shaft. The device comprises a base, a lever and a needle bed. The needle bed is attached to one of the base and the lever and is configured to support, substantially in a predefined position, a shaft carrying a biological tissue. The other one of the base and the lever is configured to support a sample holder attached thereto. The lever is movable between settings relative to the base, and a sample holder suitably attached to the device is thereby movable relative to the needle bed, so that in a first setting the sample holder and the needle bed are distant from one another. In a second setting the sample holder and the needle bed are situated proximal to one another having a predefined arrangement relative to one another.

According to some embodiments the device of '095 may be employed to transfer a biopsy sample from the shaft (e.g. biopsy needle) onto a sample holder such as a cassette assembled with a sample sheet having an adhering surface. Such a transfer may maintain the orientation of the biopsy sample as is explained in '095. For example, when lever of the device is lifted (namely, being in an open position), an assembled cassette comprising a sample sheet may be attached to the lever. A biopsy gun carrying a sample tissue in the exposed notch of the needle (the cannula is pulled back) may be placed and secured in a gun house of the device, so that the needle may be supported on a needle bed. The lever may be lowered until it is stopped by a stopper, thereby pressing the sample sheet in the cassette onto the sample tissue on the needle and attaching the sample tissue to the sample sheet. The lever may then be lifted, thereby detaching the sample from the notch and leaving the sample on the sample sheet. The cassette may then be disassembled from the lever, and the sample sheet carrying the sample tissue on it may be removed from the cassette. The sample sheet carrying the sample tissue may be placed in a sample box, the sample box may be closed with a sample box cover, and the closed sample box with the sample tissue on the sample sheet inside may be taken through a suitable chemical preparation process prior to examination. After the chemical preparation process, the dried sample sheet with the sample tissue thereon may be removed from the sample box and placed face down on the floor of a metal mold, so that the sample tissue touches directly the floor of the metal mold. The sample tissue may be adhered to the floor of the metal mold by slight pressing, and optionally using a drop of paraffin. The sample box may be fixed on top of metal mold, and the space within, that is to say between the metal mold and the sample box, may be filled with paraffin. After the paraffin solidifies the metal mold may be removed, leaving the sample box filled with a block of paraffin and with the sample tissue still adhered to the sample sheet, on top. The sample box with the sample tissue may then be taken for slicing. A selected slice may be placed on a first glass plate and may be heated and then cleaned with designated detergents to expel the paraffin. A second glass plate may be then attached on top of the sample tissue, so that the sample tissue may be between the first and second glass plates, and the sample tissue between two glass plates may be taken for examination, e.g. under a microscope.

It is thus noted that by employing such method of transferring the sample onto a sample holder such as a sample sheet, the shape of the sample on the scalpel or on the biopsy needle is maintained on the sample holder. Moreover, the shape of the sample may be maintained until and including the slicing step, prior to microscopic inspection. Thus, according to some embodiments, a first image of the sample may be obtained soon after obtaining the sample tissue, for example when the sample tissue is still supported on a biopsy needle or on a scalpel etc. Or, additionally or alternatively, a first image may be obtained soon after transferring the sample onto a sample holder such as a sample sheet as described above. A second image may then be obtained following any desired step in the process of preparing the sample to microscopic inspection described above. For example, a second image may be obtained soon before slicing the sample for the microscopic inspection, or after such slicing, or soon after the microscopic inspection. Because the shape of the sample is maintained, the sample being adhered to the sample holder or the sample sheet throughout the chemical process and until slicing, a first image and a second image of the sample will be similar to each other, whereas a first image of one sample and a second image of another sample will most probably be different from one another. In some embodiments a comparison of a second image may be carried out to a particular contour in a map generated from a first image, such as contour 154a or 154b in FIG. 2B above. In some samples having thickness variations, a particular slice may deviate significantly in shape from the shape of the entire sample. It may therefore be required, in some embodiments, to compare an the second image (or a contour generated therefrom) to a contour in a topographical map, such as map 152, representing a cross section at an altitude that is equal to that of the slice imaged in the second image.

According to some embodiments the biopsy sample may be dyed prior to obtaining the first image. Dyeing the biopsy sample may be carried out using dyes resilient to chemical processes that the sample is exposed to prior slicing and inspection. Hence, such dyeing substantially appears similar in the first image and in the second image, thereby increasing the confidence associated with the comparison between the two images. The biopsy sample may be dyed according to a code that is unique to each patient. For example, all biopsy samples obtained from a same patient are colored according to a same code but samples from different patients (of the same day or of the same week etc.) are dyed according to different codes. A dyeing code may involve location of marks on the sample, e.g. as in a bar-code or may involve color code or any combination thereof. After the first image is obtained, the biopsy sample is processed in preparation for sectioning, or slicing, to obtain thin slices of the sample for inspection e.g. using a microscope. Such preparation process may include immersion of the sample in neutral buffered formaldehyde preservative solution, in ethanol, in xylene and in VIP paraffin; drying the sample; embedding the sample in a paraffin bulk, and slicing the paraffin bulk to obtain thin slices of paraffin containing slices of the sample. The paraffin may then be melted and cleaned, and the sample slice may be taken for inspection.

According to some embodiments, a second image of the sample is obtained prior to sectioning the paraffin bulk embedding the sample. The paraffin bulk is suitably positioned under a second camera with the surface including the sample facing upwards towards the second camera, so that an image obtained by the second camera includes a view of the sample. According to some embodiments, a second image of the sample is obtained after slicing the paraffin bulk, and after cleaning the paraffin from the obtained slice. For example, a paraffin slice comprising a sample slice therein is placed on a glass plate, the glass plate is then heated to melt the paraffin, and the molten paraffin is cleaned away. The glass plate carrying the sample slice thereon is suitably placed under a second camera and a second image of the sample is obtained using the second camera.

According to some embodiments the first image and the second image of the sample are then compared. According to some embodiments a similarity in shape of the samples imaged in the first and second images indicates that the images are of a same sample, thereby validating the source of the samples and the identity thereof. Comparing the first and second images may be carried out by a trained person that views the two images and decides whether the two images are of a same sample. Alternatively or additionally, a computerized comparison may be carried out. For example, each image may be transferred to processing unit 104 comprising an image processing module 106 of FIG. 1 or FIG. 4. Image processing module 106 may then generate a map of each imaged sample, substantially according to the description above of FIG. 2 and FIG. 6. Such generated maps may comprise a contour outlining the border of each of the imaged samples in the first and the second images. The two obtained contours may then be compared by processing unit 104, e.g. by applying known methods of obtaining a best fit between shapes. For example, a characteristic of the obtained maps may be compared. A characteristic of the obtained maps may include for example a length of the contoured shape as described in FIG. 6B, a width thereof, a total length of the circumference of the contour, a total area enclosed within each contour, and any combination thereof. A characteristic of the two shapes may then be compared, resulting in a test result indicating the degree of similarity of the two shapes, and indicating the degree of similarity of the first image to the second image. A direct comparison may be obtained for example by an RMS measure of the distances between the two contours when the two contours are positioned to fit best one to the other, namely the first to the second. A low RMS result may indicate a high degree of similarity and vice versa. The fit result may then be compared to a pre-determine fit threshold to validate or disprove the identity of the obtained sample.

According to some embodiments, obtaining at least one of the first image and the second image is carried out by an imaging device other than a camera. According to some embodiments, at least one of the first image and the second image is carried out by an imaging device selected from the group consisting of MRI, X-ray, Doppler imaging and scanning laser beam.

Thus, according to an aspect of some embodiments there is provided a system 100, 140 for facilitating obtaining a biopsy sample from a body of a patient. The system comprises a display 102 for displaying images to a user, a processing unit 104 comprising an image processing module 106, functionally associated with the display, and a camera 110. The camera is functionally associated with the processing unit through a communication channel 114 for transferring images from the camera to the processing unit. The camera is configured to obtain images of a biopsy sample 112 obtained from the body of a patient.

The processing unit is configured to receive image data from an imaging modality 120 capable of obtaining images of internal patient's body parts not directly visible from outside the body, and to display to a user on the display 102 images related to the image data. The processing unit is further configured to generate, from at least one image of a biopsy sample and using the image processing module 106, a processed image related to the biopsy sample, and to display on the display 102 the processed image.

According to some embodiments, the image processing module is configured to generate a map 152, 156 of the biopsy sample 112 from an image 150a of the biopsy sample received from the camera. According to some embodiments, the map 152 represents topographic variations of the biopsy sample. According to some embodiments, the map 156 represents material variations of the biopsy sample. According to some embodiments, the image processing module is configured to generate a virtual 3D model of the biopsy sample.

According to some embodiments, the image processing module is configured to identify a border of the biopsy sample on an image of a biopsy sample received from the camera. According to some embodiments, the image processing module is configured to generate from an image of a biopsy sample received from the camera a contour 154*a* substantially outlining the border of the biopsy sample on the image. According to some embodiments, the image processing module is configured to generate from an image 150*b* received from the camera of a biopsy sample broken to pieces, a multitude of separate contours 158*a*, 158*b* wherein each such contour substantially outlines the border of one piece of the biopsy sample on the image. According to some embodiments, the processing unit is configured to receive a mark or a multitude of marks, virtually marked by a user on the image of the biopsy sample, and to employ such marks in the generation of the contours.

According to some embodiments, the camera 110 is a stills camera. According to some embodiments, the camera is a video camera. According to some embodiments, the camera is mechanically attached to a stand 116, 182, the stand being configured to support a biopsy sample 112 so that the camera is aimed to the biopsy sample to obtain an image thereof. According to some embodiments, the stand 182 is configured to support a biopsy needle 172 at a pre-defined position so that the camera is aimed to the biopsy needle to obtain an image of a biopsy sample 112 carried on the biopsy needle.

According to some embodiments, the camera is fixedly attached to the stand. According to some embodiments, the stand comprises a groove 136 or the stand is otherwise configured to enable attachment of the camera in several orientations, thereby the camera being configured to obtain images of a biopsy sample from several directions.

According to some embodiments, the system 100 comprises a length scale 138 positioned proximal to the biopsy sample, thereby allowing an image of the biopsy sample to incorporate a length scale. According to some embodiments, the processing unit is configured to determine a dimension of the imaged biopsy sample. According to some embodiments, the dimension is a length of the biopsy sample and/or a width of the biopsy sample.

According to some embodiments, the communication channel 114 is unidirectional, enabling transferring images from the camera to the processing unit 104. According to some embodiments, the communication channel is bidirectional, enabling transferring images from the camera to the processing unit and to transfer commands from the processing unit to the camera. According to some embodiments, the camera the communication channel comprises wired electronic connection for transferring images from the camera to the processing unit. According to some embodiments, the communication channel comprises wireless connection to the processing unit for transferring images from the camera to the processing unit.

According to some embodiments, the processing unit is configured to extract from an image 200 of a biopsy sample received from the camera a distance, e.g. d1 or d2 between a landmark of a biopsy sample 172 and a landmark (e.g. 226*a*, 226*b*, 228) of the biopsy needle.

According to some embodiments, system 100 is functionally associated with an imaging modality 120 capable of obtaining images of internal patient's body parts not directly visible from outside the body. According to some embodiments, system 100 comprises an imaging modality capable of obtaining images of internal patient's body parts not directly visible from outside the body. According to some embodiments, the imaging modality comprises an ultrasonography module. According to some embodiments, the imaging modality comprises a magnetic resonance imaging (MRI) module. According to some embodiments, the imaging modality comprises an X-ray imaging module.

According to some embodiments, the processing unit 104 further comprises a 3D modelling module 108 configured to receive image data provided by an imaging modality such as imaging modality 120. The image data may be assigned with corresponding image position data along pre-selected coordinates, and the 3D modelling module 108 is configured to create a virtual 3D model of an organ using suitably selected image data, assigned with image position data, of the organ.

According to some embodiments, system 140 further comprises a tracking system 160 functionally associated with at least one tracking sensor 162. The tracking system is functionally associated with the processing unit 104 and configured to provide to the processing unit position data comprising location and orientation of the tracking sensors 162 along pre-selected coordinates 164 substantially in real time.

According to some embodiments, the imaging modality comprises an imaging probe 122 and a tracking sensor 162*a* has a known spatial relation with the imaging probe, thereby providing the processing unit position data substantially of the imaging probe. According to some embodiments, the imaging probe comprises a trans-rectal ultrasound imaging probe.

According to some embodiments, the processing unit 104 is further configured to assign image position data corresponding to position data of the imaging probe 122 received from the tracking system 160, to image data received from the imaging modality 120.

According to some embodiments, the imaging probe 122 is configured to mechanically attach to a biopsy needle 172 thereby having at least partially known spatial relation with the biopsy needle, so that the tracking sensor 162*a* has at least partially known spatial relation with the biopsy needle. According to some embodiments, the at least partially known spatial relation between the tracking sensor and the biopsy needle is fixed. In some embodiments the spatial relation between the tracking sensor and the biopsy needle does not vary in time.

According to some embodiments, the processing unit is configured to generate a combined image that may be displayed on display 102, comprising image data received from the imaging modality and a synthetic mark indicating a location of the biopsy needle. According to some embodiments, a location of the synthetic mark on the combined image relative to the image data received from the imaging modality is dependent on a position of the biopsy needle received by the processing unit from the tracking system.

According to some embodiments, the processing unit further comprises a 3D modelling module 108 configured to receive image data provided by an imaging modality such as imaging modality 120, the image data being assigned with corresponding image position data. The 3D modelling module is further configured to create a virtual 3D model of an organ using suitably selected image data, assigned with image position data, of the organ.

According to some embodiments, a tracking sensor of the tracking system has at least partially known spatial relation with a biopsy needle. According to some embodiments, the biopsy needle is configured to obtain a biopsy sample of the prostate. According to some embodiments, the at least partially known spatial relation between the tracking sensor and the biopsy needle is fixed. According to some embodiments, the processing unit is configured to generate a combined image comprising image data received from the imaging modality and a synthetic mark indicating a location of the biopsy needle. According to some embodiments the combined image comprises a 3D image of an organ. According to some embodiments the 3D image is generated from a series of 2D images of the organ, obtained by the imaging modality. According to some embodiments, a location of the synthetic mark on the combined image that displays image data received from the imaging modality, is dependent on a position of the biopsy needle 172 received by the processing unit from the tracking system 160.

According to some embodiments, the processing unit is configured to generate a combined image comprising a virtual 3D model of an organ generated by the 3D modelling module 108, and a synthetic mark indicating a location of the biopsy needle. According to some embodiments, a location of the synthetic mark on the combined image relative to the virtual 3D model is dependent on a position of the biopsy needle received by the processing unit from the tracking system.

According to some embodiments, the processing unit is configured to generate a combined image comprising a virtual 3D model of an organ generated by the 3D modelling module, and a synthetic mark indicating a location in the organ from which the biopsy sample was obtained. According to some embodiments, the processing unit is configured to generate a combined image comprising a virtual 3D model of an organ generated by the 3D modelling module, and a scaled image of the biopsy sample positioned in the combined image so as to indicate a location in the organ from which the biopsy sample was obtained.

According to an aspect of some embodiments there is provided a method of processing a biopsy sample. The method comprises providing a system for facilitating obtaining a biopsy sample from a body of a patient such as system 100 or system 140 as described above. The method further comprises providing a biopsy sample 112 obtained from a body of a patient. The method further comprises obtaining an image of the biopsy sample using the camera. The method further comprises transferring an image of the biopsy sample obtained by the camera to the processing unit 104 of the system. The method further comprises displaying an image related to the biopsy sample and obtained from the processing unit on the display 102 of the system.

According to some embodiments, the method further comprises processing at least one image of a biopsy sample by the image processor module to obtain the image related to the biopsy sample. According to some embodiments, the step of processing an image of a biopsy sample includes obtaining a map of the biopsy sample. According to some embodiments, the map represents topographic variations or material variations of the biopsy sample.

According to some embodiments, the processing step includes generation of a virtual 3D model of the biopsy sample. According to some embodiments, the processing includes identifying a border of the biopsy sample on an image thereof. According to some embodiments, the processing further includes generating from an image of a biopsy sample a contour substantially outlining the border of the biopsy sample. According to some embodiments, the processing further includes generating from an image of a biopsy sample broken to pieces, a multitude of separate contours wherein each such contour substantially outlines the border of one piece of the biopsy sample on the image.

According to some embodiments, the generation step of a virtual 3D model of the biopsy sample is assisted by a mark, virtually marked by a user on the image of the biopsy sample.

According to some embodiments, the providing step of a biopsy sample includes providing a biopsy sample supported on a biopsy needle. According to some embodiments, the method further comprises processing by the image processor module at least one image of a biopsy sample supported on a biopsy needle. According to some embodiments, the method further comprises extracting from an image of a biopsy sample supported on a biopsy needle a distance between a landmark of a biopsy sample and a landmark of the biopsy needle. According to some embodiments, the landmark of the biopsy sample is a portion of a border of the biopsy sample.

According to some embodiments of the method, the landmark of the biopsy needle is selected from the group consisting of the needle distal tip and a portion of the needle notch. According to some embodiments of the method, at least one of the landmarks of the biopsy sample and the biopsy needle is virtually marked by a user on the image.

According to some embodiments of the method, the extracting step of a distance includes establishing a scale of the image of the biopsy sample from known spatial relation between a position of the camera and a position of the biopsy sample. According to some embodiments of the method, the extracting step of a distance includes establishing a scale of the image of the biopsy sample from a length scale positioned proximal to the biopsy sample to be imaged in the image.

According to some embodiments of the method, the displaying step includes displaying a combined image comprising image data received from an imaging modality capable of obtaining images of internal patient's body parts not directly visible from outside the body, and a synthetic mark indicating a location in the organ from which the biopsy sample was obtained. According to some embodiments of the method, the displaying includes displaying a combined image comprising a virtual 3D model of an organ, and a synthetic mark indicating a location in the organ from which the biopsy sample was obtained.

According to an aspect of some embodiments there is provided a method of processing a biopsy sample. The method comprises providing a biopsy sample obtained from a body of a patient. The method further comprises obtaining a first image of the biopsy sample. The method further comprises obtaining a second image of the biopsy sample. The method further comprises comparing image data obtained from the first image to image data obtained from the second image. The method may thereby validate or disprove the identity of the biopsy sample.

According to some embodiments the method further includes a step of transferring the biopsy sample from a scalpel or a biopsy needle to a sample holder so that a shape of the biopsy sample on the scalpel or on the biopsy needle is maintained on the sample holder. According to some embodiments the transferring step is performed after the step of obtaining the first image and the first image is obtained when the biopsy sample is on the sample holder.

According to some embodiments the method further includes a step of chemically treating the biopsy sample, performed after obtaining the first image and before obtaining the second image. According to some embodiments the method further includes a step of sectioning the biopsy sample performed after obtaining the first image and before obtaining the second image.

According to some embodiments the step of obtaining a first image of the biopsy sample and the step of obtaining a second image of the biopsy sample are carried out using different cameras.

According to some embodiments the method further includes a step of dyeing the biopsy sample, performed prior to the step of obtaining a first image of the biopsy sample.

According to some embodiments the biopsy sample is a biopsy sample.

According to some embodiments the method further includes processing the first image and the second image to generate a map from the image data of each image, wherein the comparing step includes comparing the map obtained from the first image to the map obtained from the second image. According to some embodiments the maps represent topographic variations or material variations of the biopsy samples. According to some embodiments the maps represent colour variations of the biopsy samples. According to some embodiments the maps include a contour substantially outlining the border of an imaged biopsy sample.

According to some embodiments the processing step of an image of a biopsy sample broken to pieces includes generating a multitude of separate contours wherein each such contour substantially outlines the border of one piece of an imaged biopsy sample. According to some embodiments the contour generation is assisted by a mark, virtually marked by a user on an image of a biopsy sample.

According to some embodiments at least one of the cameras is a stills camera. According to some embodiments at least one of the cameras is a video camera.

According to some embodiments the comparing step generates a measure of fit which is determined by the degree of similarity between characteristics of the first image and characteristics of the second image. characteristics the method further includes a step of comparing the generated measure of fit to a fit threshold, wherein the validating or disproving the identity of the biopsy sample is determined by the results of the comparison of the generated measure of fit to the fit threshold. According to some embodiments the method further includes a step of reporting the validation or disproving of an identity of the imaged biopsy sample, based on the results of the comparison of the generated measure of fit to the fit threshold.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. No feature described in the context of an embodiment is to be considered an essential feature of that embodiment, unless explicitly specified as such.

Although steps of methods according to some embodiments may be described in a specific sequence, methods of the invention may comprise some or all of the described steps carried out in a different order. A method of the invention may comprise all of the steps described or only a few of the described steps. No particular step in a disclosed method is to be considered an essential step of that method, unless explicitly specified as such.

Although the invention is described in conjunction with specific embodiments thereof, it is evident that numerous alternatives, modifications and variations that are apparent to those skilled in the art may exist. Accordingly, the invention embraces all such alternatives, modifications and variations that fall within the scope of the appended claims. It is to be understood that the invention is not necessarily limited in its application to the details of construction and the arrangement of the components and/or methods set forth herein. Other embodiments may be practiced, and an embodiment may be carried out in various ways.

The phraseology and terminology employed herein are for descriptive purpose and should not be regarded as limiting. Citation or identification of any reference in this application shall not be construed as an admission that such reference is available as prior art to the invention. Section headings are used herein to ease understanding of the specification and should not be construed as necessarily limiting.

The invention claimed is:

1. A system for facilitating obtaining a biopsy sample from a body of a patient, the system comprising:
   a. a display for displaying images to a user;
   b. a processing unit including an image processing module, functionally associated with said display;
   c. a tracking system functionally associated with at least one tracking sensor having a known spatial relation with an imaging probe of an imaging modality capable of obtaining images of internal patient's body parts not directly visible from outside said body, and having a known spatial relation with a biopsy needle, said tracking system being functionally associated with said processing unit and configured to provide to said processing unit position data including location and orientation of said at least one tracking sensor along pre-selected coordinates substantially in real time; and
   d. a camera functionally associated with said processing unit through a communication channel for transferring images from said camera to said processing unit, said camera being configured to obtain images of a biopsy sample obtained from said body of a patient;
   e. wherein said camera is mechanically attached to a stand and said stand is configured to support a biopsy sample so that said camera is aimed to said biopsy sample to obtain an image thereof;
   f. wherein said stand is further configured to support a biopsy needle at a pre-defined position so that said camera is aimed to said biopsy needle to obtain an image of a biopsy sample carried thereon;
   wherein said processing unit is configured to,
      receive image data from the imaging modality;
      assign image position data corresponding to position data of said imaging probe received from said tracking system, to image data received from said imaging modality;
      assign image position data corresponding to position data of said biopsy needle received from said tracking system, to images received from said camera; and
      generate, from at least one image of a biopsy sample and using said image processing module, a combined image including image data received from said imaging modality and a processed image related to said biopsy sample, and to display on said display said combined image.

2. The system of claim 1 wherein said camera is configured to obtain images of a biopsy sample from several directions.

3. The system of claim 1, further comprising a length scale positioned proximal to said biopsy sample, thereby allowing an image of said biopsy sample to incorporate a length scale.

4. The system of claim 3 wherein said processing unit is configured to determine at least one dimension, selected from the group consisting of length and width, of said imaged biopsy sample.

5. The system of claim 1 wherein said communication channel is bidirectional, enabling transferring images from said camera to said processing unit and to transfer commands from said processing unit to said camera.

6. The system of claim 1, wherein said imaging modality includes at least one member selected from the group consisting of an ultrasonography module, a magnetic resonance imaging (MRI) module, and an X-ray imaging module.

7. The system of claim 1 wherein said imaging modality includes a trans-rectal ultrasound imaging probe.

8. The system of claim 1 wherein said processing unit is configured to generate a combined image including image data received from said imaging modality and a synthetic mark indicating a location of said biopsy needle.

9. The system of claim 1 wherein said processing unit further includes a 3D modelling module configured to receive image data provided by an imaging modality, said image data being assigned with corresponding image position data, and said 3D modelling module is further configured to create a virtual 3D model of an organ using suitably selected image data, assigned with image position data, of said organ.

10. The system of claim 9 wherein said processing unit is configured to generate a combined image including a virtual 3D model of an organ generated by said 3D modelling module, and a synthetic mark indicating a location of said biopsy needle.

11. The system of claim 9 wherein said processing unit is configured to generate a combined image including a virtual 3D model of an organ generated by said 3D modelling module, and a scaled image of said biopsy sample positioned in said combined image so as to indicate a location in said organ from which said biopsy sample was obtained.

12. The system of claim 1 wherein said processing unit is configured to extract from an image of the biopsy sample received from said camera a distance between a landmark of the biopsy sample and a landmark of said biopsy needle.

13. The system of claim 12 wherein said landmark of a biopsy needle is selected from the group consisting of a needle distal tip of the biopsy needle and a portion of a needle notch of the biopsy needle.

14. A method of processing a biopsy sample, the method comprising:
    receiving image data from an imaging modality, the image data being related to images of an internal patient's body part not directly visible from outside the body;
    using a biopsy needle, obtaining the biopsy sample from the internal body part of the patient;
    obtaining an image of the biopsy sample using a camera;
    processing the image of the biopsy sample to obtain a map of the biopsy sample;
    using a tracking system functionally associated with at least one tracking sensor having a known spatial relation with an imaging probe of the imaging modality, and having a known spatial relation with the biopsy needle:
    i. assigning image position data corresponding to position data of the imaging probe received from the tracking system, to image data received from the imaging modality,
    ii. assigning image position data corresponding to position data of the biopsy needle received from the tracking system, to images received from the camera, and
    generating a combined image including image data received from the imaging modality and a processed image related to the biopsy sample, and displaying the combined image on a display.

15. The method of 14 wherein said processing includes generation of a virtual 3D model of said biopsy sample.

16. The method of claim 14 wherein said processing includes identifying a border of said biopsy sample on an image thereof.

17. The method of claim 16 wherein said processing further includes generating from an image of a biopsy sample broken to pieces, a multitude of separate contours wherein each of the multitude of separate contours substantially outlines the border of one piece of the biopsy sample on the image.

18. The method of claim 14, further comprising obtaining a next biopsy sample from the patient, based on considering the combined image.

* * * * *